(12) United States Patent
St. Anne

(10) Patent No.: US 9,408,943 B2
(45) Date of Patent: *Aug. 9, 2016

(54) METHOD AND DEVICE FOR FEMALE URINARY INCONTINENCE

(71) Applicant: ParaPatch, Inc., Inglewood, CA (US)

(72) Inventor: Cora St. Anne, Inglewood, CA (US)

(73) Assignee: ParaPatch, Inc., Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/207,259

(22) Filed: Mar. 12, 2014

(65) Prior Publication Data
US 2014/0194550 A1 Jul. 10, 2014

Related U.S. Application Data

(63) Continuation of application No. 12/999,114, filed as application No. PCT/US2010/033349 on May 3, 2010, now Pat. No. 8,684,008.

(60) Provisional application No. 61/181,556, filed on May 27, 2009.

(51) Int. Cl.
*A61L 24/04* (2006.01)
*A61F 2/00* (2006.01)
*A61F 13/472* (2006.01)
*A61F 13/15* (2006.01)

(52) U.S. Cl.
CPC ............... *A61L 24/04* (2013.01); *A61F 2/0009* (2013.01); *A61F 13/47209* (2013.01); *A61F 2013/15097* (2013.01)

(58) Field of Classification Search
CPC ....... A61F 2/0054; A61F 5/48; A61F 2/0009; A61F 2/0022; A61F 2/0013; A61F 6/04; A61F 6/065; A61F 5/41; A61F 6/24; A61F 6/22; A61F 6/20; A61F 2006/047; A61F 2006/048; A61F 5/453; A61F 13/471; A61F 5/4401; A61F 5/443; A61B 17/11; A61B 10/0058
USPC .......... 128/885, 842–844, 893, 887, DIG. 25; 602/48, 58; 604/349, 352, 385.17; 24/DIG. 11

See application file for complete search history.

(56) References Cited

U.S. PATENT DOCUMENTS

| | | |
|---|---|---|
| 3,646,616 A | 3/1972 | Keshin |
| 3,762,415 A | 10/1973 | Morrison |
| 3,789,828 A | 2/1974 | Schulte |

(Continued)

OTHER PUBLICATIONS

"Incontinence—Urinary Leakage—A Common and Treatable Condition" Pamphlet, Kaiser Permanente (1995) in 11 pages.

(Continued)

*Primary Examiner* — Ophelia A Hawthorne
(74) *Attorney, Agent, or Firm* — Knobbe, Martens Olson & Bear, LLP

(57) ABSTRACT

A method and device for use in stress female urinary incontinence. A small, flexible adhesive patch is applied directly to the clitoris of a person suffering from stress female urinary incontinence. The adhesive is of a type sufficient to stimulate the mechanoreceptors located in the clitoris whereby to inhibit discharge from the bladder. The patch is formed of a backing sheet of an impervious material containing adhesive on one side. A release liner prevents the adhesive from drying out.

23 Claims, 2 Drawing Sheets

(56) References Cited

U.S. PATENT DOCUMENTS

| | | | |
|---|---|---|---|
| 3,905,372 A | 9/1975 | Denkinger | |
| 3,911,173 A | 10/1975 | Sprague, Jr. | |
| 3,929,135 A | 12/1975 | Thompson | |
| 4,191,609 A | 3/1980 | Trokhan | |
| 4,324,246 A | 4/1982 | Mullane et al. | |
| 4,342,314 A | 8/1982 | Radel et al. | |
| 4,367,732 A | 1/1983 | Poulsen et al. | |
| 4,463,045 A | 7/1984 | Ahr et al. | |
| 4,486,193 A * | 12/1984 | Shaw et al. | 424/449 |
| 4,573,986 A | 3/1986 | Minetola et al. | |
| 4,610,678 A | 9/1986 | Weisman et al. | |
| 4,782,535 A | 11/1988 | Yewer, Jr. et al. | |
| 4,785,996 A | 11/1988 | Ziecker et al. | |
| 4,822,347 A | 4/1989 | MacDougall | |
| 4,834,735 A | 5/1989 | Alemany et al. | |
| 4,842,666 A | 6/1989 | Werenicz | |
| 4,846,819 A | 7/1989 | Welch | |
| 4,850,986 A | 7/1989 | Temple | |
| 4,875,898 A | 10/1989 | Eakin | |
| 4,892,535 A | 1/1990 | Bjornberg et al. | |
| 4,917,697 A | 4/1990 | Osborn, III et al. | |
| 4,920,986 A | 5/1990 | Biswas | |
| 4,944,734 A | 7/1990 | Wallach | |
| 4,950,264 A | 8/1990 | Osborn, III | |
| 5,006,394 A | 4/1991 | Baird | |
| 5,007,894 A | 4/1991 | Enhorning | |
| 5,074,855 A | 12/1991 | Rosenbluth et al. | |
| 5,090,424 A | 2/1992 | Simon et al. | |
| 5,131,906 A | 7/1992 | Chen | |
| 5,263,947 A | 11/1993 | Kay | |
| 5,312,384 A | 5/1994 | Temple | |
| 5,336,208 A | 8/1994 | Rosenbluth et al. | |
| 5,383,867 A | 1/1995 | Klinger | |
| 5,386,836 A | 2/1995 | Biswas | |
| 5,417,226 A | 5/1995 | Juma | |
| 5,509,427 A | 4/1996 | Simon et al. | |
| 5,513,659 A | 5/1996 | Buuck et al. | |
| 5,589,978 A | 12/1996 | Fantone | |
| 5,669,395 A | 9/1997 | Thompson | |
| 5,693,002 A * | 12/1997 | Tucker et al. | 600/38 |
| 5,804,215 A | 9/1998 | Cubbage et al. | |
| 5,843,011 A | 12/1998 | Lucas | |
| 5,877,216 A * | 3/1999 | Place et al. | 514/573 |
| 6,131,575 A | 10/2000 | Lenker et al. | |
| 6,179,775 B1 * | 1/2001 | Thompson | A61H 19/34 600/38 |
| 6,224,541 B1 * | 5/2001 | Thompson | 600/38 |
| 6,461,340 B1 * | 10/2002 | Lenker et al. | 604/385.17 |
| 6,593,313 B2 | 7/2003 | Place et al. | |
| 6,836,684 B1 | 12/2004 | Rijkhoff et al. | |
| 6,949,067 B1 | 9/2005 | Dann et al. | |
| 6,964,643 B2 * | 11/2005 | Hovland | A61F 5/48 601/6 |
| 7,565,198 B2 | 7/2009 | Bennett et al. | |
| 8,684,008 B2 * | 4/2014 | St. Anne | 128/885 |
| 2002/0055761 A1 | 5/2002 | Mann et al. | |
| 2004/0242770 A1 * | 12/2004 | Feldstein et al. | 525/54.3 |
| 2009/0118574 A1 * | 5/2009 | Stephenson | A41B 9/04 600/38 |
| 2013/0184778 A1 | 7/2013 | St. Anne et al. | |

OTHER PUBLICATIONS

"The selling of incontinence." Consumer Reports Oct. 1997 in 3 pages.

Document of record in the filed of parent U.S. App. No. 12/999,114 (now U.S. Pat. No. 8,684,008) filed Nov. 14, 2013 entiteld "Activites of inventor Cora St. Anne described in the accompanying Information Disclosure Statement Transmittal submitted herewith on Nov. 14, 2013 in 6 pages."

Akala et al. "Novel pH-sensitive hydrogels with adjustable swelling kinetics." Biomaterials, Jun. 1998, 19(11-12) 1037-47.

Baron J: Partial androgen insensitivity syndrome: Ginekologia Polska, Jun. 1994, 65(6):319-25. (Abstract only) in 1 page.

Baron, J.: Classical and Incomplete Androgen Insensitivity Syndromes; Ginekologia Polska, Jul. 1994, 65(7):377-86. (Abstract only) in 1 page.

Benzl JS: Vaginal dysfunction; in Benson JT (ed): Female Pelvic Floor Disorders. Norton, 1992, Chapter 13, pp. 307-311 in 5 pages.

Bond, SJ; Seibel, N; Kapur, S; Newman, KD: Rhabdomyosarcoma of the clitoris; Cancer, Apr. 1, 1994, 73(7): 1984-6. (Abstract only) in 1 page.

Chalker et al. Overcoming Bladder Disorders. Harper and Row (1990) pp. 3, 44, and 45 in 3 pages.

Chapter 11, "Sphincter Electromyography and Other Electrophysiological Tests" in Hald et al.: The Urinary Bladder, Neurology and Dynamics; Williams & Wilkins (1982), pp. 118-127 in 10 pages.

Chapter 12, "Uroflowmetry and Pressure-flow Investigations" in Hald et al.: The Urinary Bladder, Neurology and Dynamics; Williams & Wilkins (1982), pp. 128-140 in 13 pages.

Chapter 13, "Urethral Closure Pressure Profile," in Hald et al.: The Urinary Bladder, Neurology and Dynamics; Williams & Wilkins (1982), pp. 141-150 in 10 pages.

Chapter 16, "Urinary Incontinence," in Hald et al.: The Urinary Bladder, Neurology and Dynamics; Williams & Wilkins (1982), pp. 175-203 in 29 pages.

Chapter 22, "Pitfalls and Errors in Urodynamic Assessment," in Hald et al.: The Urinary Bladder, Neurology and Dynamics; Williams & Wilkins (1982), pp. 310-329 in 20 pages.

Chapters 1 and 2 in Hald et al.: The Urinary Bladder, Neurology and Dynamics; Williams & Wilkins (1982), pp. ix-21 in 22 pages.

Chapters 3 and 4, pp. 22-47 of "The Urinary Bladder—Neurology and Dynamics," Lippincott (1982) in 28 pages.

Colleselli K et al. The female urethral sphincter: a morphological and topographical study. J Urology Jul. 1998, 160 (1): 49-54. (Abstract only) in 1 page.

Dahms et al. "The impact of sacral root anatomy on selective electrical stimulation for bladder evacuation." World J. Urology, 1998, 16(5): 322-8 (Abstract only) in 1 page.

Dasgupta,, P; Haslam, C; Goodwin, R; Fowler, CJ; The 'Queen Square bladder stimulator': a device for assisting emptying of the neurogenic bladder: British Journal of Urology, Aug. 1997, 80(2):234-7. (Abstract only) in 1 page.

de Groat. Anatomy of the central neural pathways controlling the lower urinary tract. European Urology 1998, 34 Suppl. 1:2-5 in 4 pages.

Deindl FM et al. "Dysfunctional voiding in women: which muscles are responsible?" British J. Urology, Dec. 1998, 82(6): 814-9 (Abstract only) in 1 page.

Deplanne et al. "The adrenergic, cholinergic, and NANC nerve-mediated contractions of the female rabbit bladder neck and proximal, medial and distal urethra." British J. Pharmacology, Apr. 1998 123(8): 1517-24 (Abstract only) in 1 page.

DETROL product literature (1999) in 62 pages.

Di Benedetto, V; Di Benedetto, A; Introduction of the anterior sagittal trans-ano-rectal approach (ASTRA) as a technical variation of the Passerini-Glazel clitoro-vaginoplasty; preliminary results; Pediatria Medica E. Chirurgica, Jul.-Aug. 1997, 19(4):273-6. (Abstract only) in 1 page.

El HEMALY, AK; Mousa, LA; Stress urinary incontinence, a new concept; European Journal of Obstetrics, Gynecology, and Reproductive Biology, Sep. 1996, 68(1-2):129-35. (Abstract only) in 1 page.

Female Pelvic Floor Disorders—Investigation and Management (Benson, J.T., ed.), Norton Medical Books (1992); Chapter 11C3 by B.C. Eriksen, Electrical Stimulation, pp. 219-231 in 15 pages.

Feneley, Roger C. L., "Normal Micturition and Its Control" chapter in "Incontinence and its management," Croom Helm (1986) pp. 16-23 in 4 pages.

Fletcher, TF, Applied anatomy and physiology of the feline lower urinary tract. Veterinary Clinics of North America. Small Animal Practice, Mar. 1996, 26(2):181-96, Feb. 25, 1999 (Abstract only) in 1 page.

(56) References Cited

OTHER PUBLICATIONS

Fowler et al., Chapter 10, "Clinical Neurophysiology" in Torrens et al. "The Physiology of the Lower Urinary Tract," Springer-Verlag (1987) pp. 309-330 in 22 pages.
Franceschetti GP et al. Minimally invasive treatment of female urinary incontinence due to sphincter incompetence. Chirugia Italiana, 1998, 50(1): 17-24. (Abstract only) in 1 page.
Frauscher et al. Intraurethral ultrasound: diagnostic evaluation of the striated urethral sphincter in incontinent females. Eur. Radiol. 8, 50-53 (1998) in 4 pages.
Gartley. Managing Incontinence. Jameson Books (1985) p. 15 in 1 page.
Glavind K. Use of a vaginal sponge during aerobic exercises in patients with stress urinary incontinence. Int'l Urogynecology Journal and Pelvic Floor Dysfuction 1997; 8(6): 351-3 (Abstract only) in 1 page.
Gosling JA. "Modification of bladder structure in response to outflow obstruction and ageing." Euro. Urology, 1997, 32 Suppl 1: 9-14 (Abstract only) in 1 page.
Hajivassiliou. The development and evolution of artificial urethral sphincters. J. Med. Engineering and Technology, Jul.-Aug. 1998, 22(4): 154-9 (Abstract only) in 1 page.
Hale DS et al., Histologic analysis of needle biopsy of urethral sphincter from women with normal and stress incontinence with comparison of electromyographic findings. Am. J. Obstet. and Gyn, 1999 Fed, 180: 342-8 in 7 pages.
Hollander et al.: Pelvic floor neuropathy; in Benson JT (ed): Female Pelvic Floor Disorders. Norton, 1992, Chapter 11, pp. 185-198 in 14 pages.
Huang et al. Preservation of pudendal afferents in sacral rhizotomies. Neurosurgery, Aug. 1997, 41(2):411-5 (Abstract only) in 1 page.
Incontinence: No Longer a Reason to Stay Home. Los Angeles Times Advertising Supplement Aug. 2, 1992 in 1 page.
INTROL Bladder Neck Support Prosthesis product literature. UroMed Corporation (1997) in 6 pages.
Jarvie et al. "Novel hydrophilic cyclic monomers in hydrogel synthesis." Biomaterials, Nov. 1998, 19 (21): 1957-61 (Abstract only) in 1 page.
Khullar V et al. The urethra (IPP, MUPP, instability, LPP). European Urology, 1998, 34 Suppl 1:20-2. in 3 pages.
Kihara, K; de Groat, WC: Sympathetic efferent pathways projecting to the bladder neck and proximal urethra in the rat; Journal of the Autonomic Nervous System, Feb. 17, 1997, 62(3):134-42.
Kouichi Ota, Tadao Yanagidani, Kazuhiro Kishikawa, Yuji Yamamori, and J.G. Collins: Cutaneous Responsiveness of Lumbar Spinal Dorsal Horn Neurons is Reduced by General Anesthesia, An effect Dependent in Part on GABA-A Mechanisms; J Neurophysiol. 80: 1383-1390, (1998) in 14 pages.
Larosa et al. Valsalva leak point-pressure (LPP) and maximal urethral closure pressure (MUCP) in women with stress urinary incontinence (SUI). Archivio Italiano di Urologia, Andrologia Dec. 1997, 69(5):287-92 (Abstract only) in 1 page.
Li, P; Wilding, TJ; Kim, SJ; Calejesan, AA; Huettner, Je; Zhuo, M.:Kainate-receptor-mediated sensory synaptic transmission in mammalian spinal cord; Nature, Jan. 14, 1999 397 (6715): 161-4. (Abstract) only in 1 page.
M. I. Resnick and A. C. Novick, "Urology Secrets" (1995) Chapter 42, pp. 133-138 in 6 pages.
McLennan et al. Supine empty stress test as a predictor of low valsalva leak point pressure. Neurourology and Urodynamics 1998, 17(2): 121-7 (Abstract only) in 1 page.
Meyer et al. Stimulated pressure profile at rest: a noninvasive method for assessing urethral sphincter function. Urology Oct. 1998, 52(4): 679-84 (Abstract only) in 1 page.
Morrison, Chapter 4, "Sensations arising from the lower urinary tract" in Torrens et al. "The Physiology of the Lower Urinary Tract," Springer-Verlag (1987) pp. 89-131 in 43 pages.
Nagamatsu et al. Evaluation of clinical indexes to predict fate of pelvic nerve dysfunction. Urol. Res. 1998, 26: 319-23 in 5 pages.
National Association for Continence—Literature (1997) in 6 pages.
O'Connell et al. Anatomical relationship between urethra and clitoris. J. Urology Jun. 1998, 159(6) 1892-7. (Abstract only) in 1 page.
Olsen AL et al. Urethral sphincter needle electromyography in women: comparison of periurethral and transvaginal approaches. Neurourology and Urodynamics, 1998: 17(5) 531-5 (Abstract only) in 1 page.
Pacheco, P; Camacho, MA; Garcia, LI;Hernandez, ME; Carrillo, P; Manzo, J: Electrophysiological evidence for the nomenclature of the pudendal nerve and sacral plexus in the male rat; Brain Research, Jul. 25, 1997, 763(2):202-8. (Abstract only) in 1 page.
Park, K; Golstein, I; Andry, C; Siroky, MB; Krane, RJ; Azadzoi, KM: Vasculogenic female sexual dysfuction: the hemodynaic basis for vaginal engogement insufficiency and clitoral erectile insufficiency; International Journal of Impotence Research, Mar. 1997, 9(1):27-37. (Abstract only) in 1 page.
Prieto et al. Valsalva minimal leak point pressure: a useful approximation to type III urinary incontinence. Oct. 1998 51(8) 783-9 (Abstract only) in 1 page.
Product Literature for the Impress Softpatch by UroMed Corporation (1998) in 12 pages.
Radziszewski P et al. "The morphological aspects of the innervation of the external urethral striated sphincter."Folia Morphologca, 1995, 54(1): 1-7 (Abstract only) in 1 page.
Reliance Urinary Control Insert product literature. UroMed Corporation (1997) in 8 pages.
Roan S. "Campaign Gets Info to Incontinent Women," Los Angeles Times, Apr. 6, 1997 p. E3 in 1 page.
Rocha et al. "Impact of Pregnancy and Childbirth on Female Rats' Urethral Nerve Fibers". J. International Urogynecology vol. 18 No. 12 (2007) (Abstract only) in 1 page.
Salansky, N; Fedotchev, A; Bondar, A: Responses of the venous system to low frequency stimulation and EEG rhythms: clinical implications; Neuroscience and Biobehavioral Reviews, May 1998 22(3);395-409. (Abstract only) in 1 page.
Siltberg et al. Cough-induced leak-point pressure. Acta Obstet Gynecol Scand 77 (1998): 1000-1007 in 8 pages.
Statutory Invention Registration (SIR) No. H1602 to Brock published Oct. 1, 1996 in 8 pages.
Steg. "Urinary Incontinence", p. 266 Churchill Livingstone (1992) in 1 page.
Strohbehn, K; Quint, LE; Prince, MR; Wojno, KJ; Delancey, JO; Magnetic resonance imaging anatomy of the female urethra: adirect histologic comparison; Obstetrics and Gynecology, Nov. 1996 88(5):750-6. (Abstract only) in 1 page.
Tan et al. Female pelvic floor: endovaginal MR imaging of normal anatomy. Radiology Mar. 1998, 206(3) 777-83 (Abstract only) in 1 page.
Torrens, Chapter 9, "Urodynamics" in Torrens et al. "The Physiology of the Lower Urinary Tract," Springer-Verlag (1987) pp. 277-305 in 29 pages.
Uher et al. "Sacral reflexes: physiology and clinical application." Dis. Colon and Rectum, Sep. 1998, 41(9): pp. 1165-1177 (Abstract only) in 1 page.
Urinary Incontinence in Adults, National Institutes of Health Consensus Development Conference Statement (1988) in 18 pages.
Urinary Stress Incontinence—Awareness Encourages Women to Speak Up, Seek Help (1993), Daniel Freeman Memorial Hospital, in 1 page.
USA Weekend HealthSmart "Can I gain control?—Effective new therapies make living with incontinence easier." p. 14 (2006) in 1 page.
van Buren. "No One Needs to Live with Incontinence," Los Angeles Times, Apr. 6, 1997 p. E4 in 1 page.
Van Duin et al., A computer model of the neural control of the lower urinary tract. Neurourology and Urodynamics, 1998, 17(3): 175-96. (Abstract only) in 1 page.

(56) References Cited

OTHER PUBLICATIONS

Von Heyden et al. Neurotransmitters in the human urethral sphincter in the absence of voiding dysfuction. Urol. Res. (1998) 26: 299-310 in 13 pages.

Walker, RJ; Brooks, HL; Holden-Dye, L: Evolution and Overview of Classical Transmitter Molecules and Their Receptors; ParaSitology, 1996, 113 Suppl: S3-33. (Abstract only) in 1 page.

Wang et al. Tension-free vaginal tape. A minimally invasive solution to stress urinary incontinence in women. J. Reprod. Med. May 1998, 43(5): 429-34 (Abstract only) in 1 page.

Warrell DW: Pelvic floor neuropathy; in Benson JT (ed): Female Pelvic Floor Disorders. Norton, 1992, Chapter 9, pp. 153-165 in 13 pages.

White R. Incontinence. Encyclopedia Brittanica 1985 Medical and Health Annual pp. 335-338 in 4 pages.

Wyczolkowski M. Functional evaluation of the internal urethral sphincter in transrectal USG. Przeglad Lekarski, 1998, 55(3): 128-32. (Abstract only) in 1 page.

Yilmaz et al. Clitoral Electromyography. J. Urology 167 2:1 (2002) (Abstract only) in 2 pages.

\* cited by examiner

METHOD AND DEVICE FOR FEMALE URINARY INCONTINENCE

CROSS-REFERENCE TO RELATED APPLICATIONS

This application claims the benefit under 35 U.S.C. §120 as a continuation of U.S. patent application Ser. No. 12/999,114 having a 371(c) date of Mar. 23, 2011, which is a national stage application of PCT App. No. PCT/US10/33349 filed on May 3, 2010, which in turn claims the benefit of U.S. Provisional Patent App. No. 61/181,556 filed May 27, 2009. All of the foregoing priority applications are hereby incorporated by reference in their entireties.

FIELD OF THE INVENTION

The invention relates to a method and device for relieving or mitigating the problems associated with female urinary incontinence.

BACKGROUND OF THE INVENTION

Female urinary incontinence is a troublesome problem for many individuals and can be classified into four major categories. From least to severe:

stress incontinence, in which a slight urine loss occur due to the momentary pressure caused by sneezing, coughing, laughing, or simply lifting a heavy object;

urge incontinence, in which a strong frequent desire to void is accompanied by involuntary urination within a minute or two of the urge;

overflow incontinence, which occurs when the bladder fills beyond capacity, creating pressure which exceeds urethral resistance—no urge to urinate is present, so the bladder just overflows; and continuous incontinence, which is a conscious or unconscious urination, which is usually the result of an abnormal passage caused by surgery, trauma, or neural damage.

A number of devises have been proposed to deal with female urinary incontinence, represented by, for example, U.S. Pat. No. 5,074,855 to Rosenbluth et al., U.S. Pat. No. 6,131,575 to Lenker et al., U.S. Pat. No. 6,461,340, to Lenker et al., U.S. Pat. No. 3,789,828 to Schulte, U.S. Pat. No. 5,509,427 to Simon et al. U.S. Pat. No. 4,892,535 to Bjornberg et al., U.S. Pat. No. 6,179,775 to Thompson, U.S. Pat. No. 6,836,684 to Rijkhoff, and Statutory Invention Registration (SIR) No. H1602 to Brock, the disclosures of each of which are hereby incorporated herein by reference.

Rosenbluth et al. and both Lenker et al. patents disclose a resilient pad configured to seal against and occlude the urethral meatus, i.e., the urethral opening. These devices are described as shaped and sized to fit each individual user's anatomy, implying that the application of this device requires careful attention for a comfortable fit. Moreover, the devices are designed for individual custom fitting, calling for predetermined sizes to be trimmed individually for optimal fit, including the use in some cases of a mold of the relevant portions of the vulva taken prior to sizing the pad. A mirror or light is suggested to facilitate insertion, indicating that the devices are difficult to apply and suggests that the device may be designed for clinical use, attended by a physician or health care professional. Moreover, these devices do not appear to be designed for highly active women, e.g. running, jogging, high and low impact aerobics or any exercise where the movement of the lower torso is essential. The devices are rigid around the perimeter contributing to discomfort as used in its intended position. In addition, the complex construction and individual custom fitting indicates a probable high overall cost to the consumer.

Lenker et al. U.S. Pat. No. 6,131,575 discloses in addition to the rigid female incontinence device, a more flexible device but only for male incontinence, shown in their FIGS. 26 to 30, and which is retained on the glans of a patient's penis by an adhesive layer formed of a pressure-sensitive hydrophilic hydrogel.

The device described in Shulte's patent is a mechanical device surgically implanted for prolonged use and features a fluid flow valve which can be operated manually, in contrast to the present invention's simplicity, ease of use and temporary nature as needed at the discretion of the user. In structure, the Shulte device appears to be a rigid mechanical device with a valve. Simon et al.'s device is designed to be inserted directly inside of the urethra with an "expandable balloon at its proximal end," again, which is in total contrast to our present invention. Bjornberg et al. and Brock describe absorbent pads of the type that can be used as incontinence pads. Brock further describes a continuous layer of adhesive for securing the pad to a wearer's skin. The pads of both Bjornberg et al. and Brock are intended to cover large general areas.

Thompson describes a device to enhance clitoral stimulation during intravaginal intercourse, using a hydrophilic, non-allergenic adhesive to seat a foraminous, elongated, generally triangular shaped pad in the female vestibule to lie beneath the labia minora to support and engage the ventral aspect of the clitoris when it is engorged with blood during the arousal phase of female sexual stimulation.

Rijkhoff et al. describes a device that uses an implanted sensor and means for generating electrical pulses to stimulate nerves to inhibit contraction of the detrusor, the muscle that expels urine from the bladder. It recognizes what has been shown by investigators, that activation of afferent nerve fibres, innervating mechanoreceptors located in the clitoris, has a strong inhibitory effect on the bladder.

BRIEF SUMMARY OF THE INVENTION

The present invention provides a method and device for use in stress female urinary incontinence. Somewhat as in the electrical stimulation of mechanoreceptors located in the clitoris, the present method physically stimulates the clitoris to provide a strong inhibitory effect on the bladder, relieving stress urinary incontinence. Notwithstanding the ability to completely relieve, stress incontinence, the device is remarkably simple. Unlike prior devices, it is not an absorbent pad to catch urine, it is not a clinical device that requires help in insertion, it does not have a rigid or semi-rigid component, nor does it have projections, and is not a complicated electronic impulse generator; moreover, the device can be used in the absence of intravaginal intercourse. It is a small, flexible adhesive patch of a size that can be comfortably applied directly to the clitoris. The patch is formed of a backing sheet of an impervious film material containing adhesive on one side. A release liner prevents the adhesive from drying out.

More particularly, a method is provided for treating stress female urinary incontinence, comprising applying an adhesive directly to the clitoris of a person suffering from stress female urinary incontinence. The adhesive is of a type sufficient to stimulate the mechanoreceptors located in the clitoris whereby to inhibit discharge from the bladder, preferably a hydrophilic, non-allergenic adhesive. The adhesive is provided by the application of the adhesive layer of the above-described patch directly to the clitoris. In a more particularized embodiment, the method involves identifying persons in need of a device or a method for treating stress female urinary incontinence.

The present invention provides a simple, low cost solution to a vexing problem, making it affordable and available. It is designed to comfortably fit any human female who suffers from urinary incontinence and includes all the necessary elements that compliment comfort, ease of use and confidence. The device is produced with soft, pliable materials that allow the user to continue daily routines with no discomforts or embarrassing interruptions. The present invention is also designed to permit the user to apply the device with no assistance, whatsoever, from anyone.

This device can be produced in various sizes, e.g. small, medium and large, to accommodate the over the-counter market. It is well suited for highly active women, e.g. engaging in running, jogging, high or low impact aerobics or any exercise where movement of the lower torso is essential. The product is very portable and can be available in individually sealed and sterilized packages of multiple units, which can easily fit into the average sized purse or pouch. The cost, comfort, simplicity, portability and ease of use attributed to this device, surpasses all other products presently available in the consumer's over-the-counter market.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
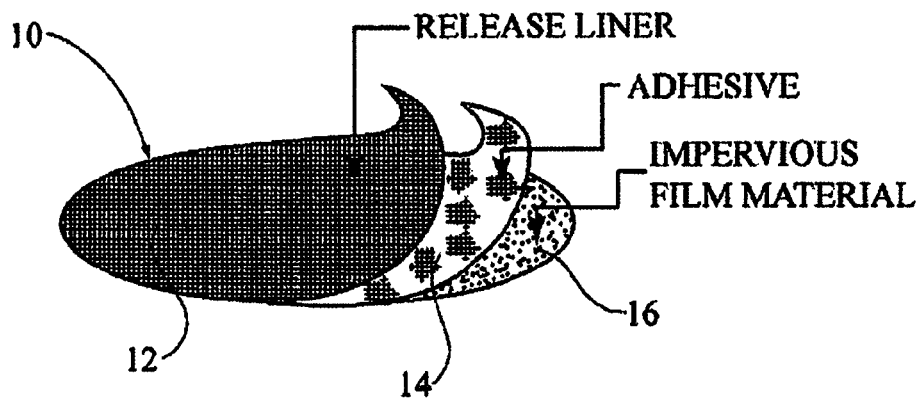
FIG. 1 is a perspective view of the device, in this embodiment having an oval shape, shown with a portion peeled up to better illustrate its construction.
Figure 2:
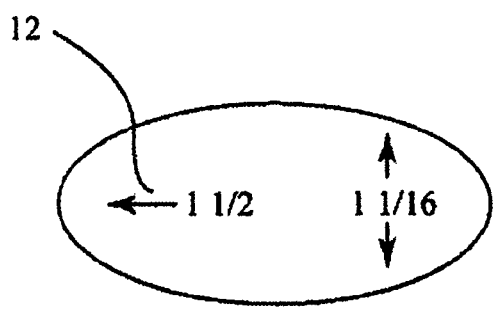
FIG. 2 is a top plan view of the device of FIG. 1.

Referring to FIGS. 1 and 2, a generally oval patch 10 of this invention is shown formed of a backing sheet 16 coated with a layer of adhesive 14 and covered with a release sheet/layer 12. The adhesive layer 14 is preferably pressure sensitive, hydrophilic and non-allergenic, as known to the art. The patch is approximately 1½ inches long and 1 1/16 inches wide.

The backing sheet 16 is preferably impervious to body fluids (e.g., urine and/or menses) and is preferably manufactures from a thin, flexible plastic film, although other flexible liquid impervious materials may also be used, all as known to the art. As used herein, the term "flexible" refers to materials which are compliant and will readily conform to the general shape and contours of clitoris region. The backing sheet 16 material may as described for the backsheet material of Brock SIR No. H1602, incorporated herein by reference, and can comprise a woven or nonwoven material, polymeric films such as thermoplastic films of polyethylene or polypropylene, or composite materials such as a film-coated nonwoven material, illustrated by a polyethylene film having a thickness of from about 0.012 mm (0.5 mil) to about 0.051 mm (2.0 mils).

The release layer/sheet 12 keeps the adhesive from drying out and can be formed of an adhesive releasing material, as known by the art, and as also illustrated in Brock SIR No. H1602. Other non-limiting examples of the adhesive releasing material/sheet includes paper, resin film, nonwoven fabric, and nonwoven fabric laminated with resin film, each having been treated with silicon. The release layer is removed before applying the patch 10.

The adhesive layer can comprise of a hydrophilic adhesive composition which may be sticky, viscous gel, or a substantially solid composition. The adhesive layer can also comprise of pressure sensitive adhesives (PSA) made from polymer such as acrylic and methacrylic ester homo- or copolymers, butyl rubber-based systems, silicones, urethanes, vinyl esters and amides, olefin copolymers, butyl rubber-based or synthetic rubbers, and the like. In another embodiment, the adhesive layer can comprise of bioadhesives (BAs), as known to the art. In contrast to PSAs that adhere mainly to dry substrates, BAs exhibit good tack when adhered to hydrated biological substrates/tissues. Non-limiting examples includes slightly cross-linked polyacrylic and polymethacrylic acids as well as blends of hydrophilic cellulose derivatives (40-95%) with polyethylene glycol. In other embodiments, the adhesive layer can comprise different combinations of PSA and BA polymeric materials of different hydrophilicity and thus different solubilities in water or in the liquids secreted by the tissue area in contact with the adhesive layer.

Regardless of the adhesive composition used, the final adhesive layer should preferably be pressure sensitive, hydrophilic and non-allergenic.

While a single patch 10 is shown in FIG. 1, in actual production and/or sale, a plurality of such patches may be formed on a single release sheet and sold as a kit whereby individual patches can be removed and applied as needed.

Figure 3:
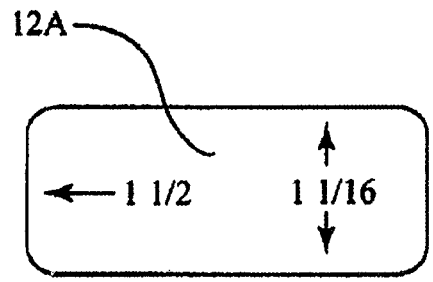
FIG. 3 is a top plan view of a device similar to the device of FIG. 1, but having a rectangular shape.

FIG. 3 shows a patch constructed in the same manner as the patch of FIG. 1, but having a generally rectangular shape) 1½ inches long and 1 and 1/16 inches wide.

Figure 4:
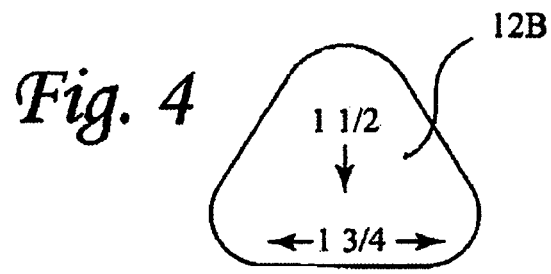
FIG. 4 is a top plan view of a device similar to the device of FIG. 1, but having a triangular shape.

FIG. 4 shows a patch constructed in the same manner as the patch of FIG. 1, but having a generally triangular shape 1 and ½ inches high and 1 and ¾ inches at its base.

Figure 5:
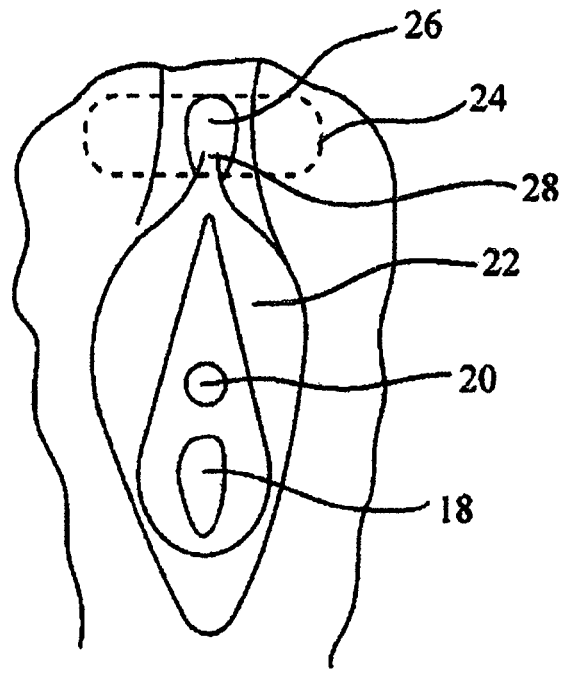
FIG. 5 is a sketch of a vagina illustrating components relevant to the invention.
Figure 6:
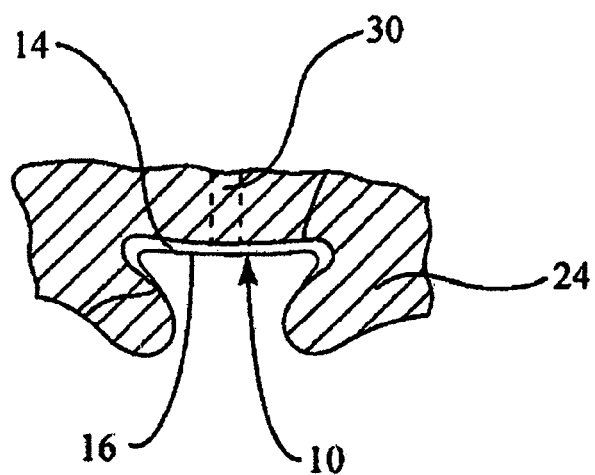
FIG. 6 is a cross-section of the clitoral region of the vagina, showing application of the patch of FIG. 1.

The patch 10 is applied with the adhesive layer directly on the clitoris. FIG. 5 is a sketch of a vagina illustrating relevant components of a vagina, including the vaginal opening 18, the urethral opening 20, the labia minora 22, the labia majora 24, the clitoral hood 26 and the clitoris at 28. Referring to FIG. 6, the patch 10 is applied between opposing folds of the labia majora 24 with the adhesive layer 14 directly contacting the clitoris 28 and covering the clitoral shaft 30. The adhesive layer 14 is protected from body fluids and, in its position, physically stimulates the clitoris 28 to provide a strong inhibitory effect on the bladder, relieving stress urinary incontinence.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

What is claimed is:

1. A patch for treating female urinary incontinence, the patch sized and configured to fit directly on and cover a clitoris without covering a urethra, the patch configured when applied to physically stimulate the clitoris to inhibit discharge from a bladder.

2. The patch of claim 1, comprising an adhesive layer on a side of the patch.

3. The patch of claim 2, wherein the adhesive layer is removably attached to a release sheet.

4. The patch of claim 2, wherein the adhesive layer comprises a pressure-sensitive adhesive.

5. The patch of claim 2, wherein the adhesive layer comprises a silicone adhesive.

6. The patch of claim 2, wherein the adhesive layer comprises a bioadhesive.

7. The patch of claim 2, wherein the adhesive layer comprises a combination of a pressure-sensitive adhesive and a bioadhesive.

8. The patch of claim 1, wherein the adhesive layer comprises a viscous gel.

9. The patch of claim 1, wherein the adhesive layer comprises a substantially solid composition.

10. The patch of claim 1, having a length of approximately 1.5 inches.

11. The patch of claim 1, wherein the patch is impervious to body fluids.

12. The patch of claim 1, wherein the patch comprises an arcuate shape.

13. The patch of claim 1, wherein the patch comprises an oval shape.

14. The patch of claim 1, wherein the patch comprises a triangular shape.

15. The patch of claim 1, wherein the patch comprises a rectangular shape.

16. A method for treating female urinary incontinence, comprising applying a flexible patch having a substantially flat skin-contacting surface directly onto a clitoris of a person suffering from female urinary incontinence, wherein applying the patch is sufficient to mechanically stimulate the clitoris, thereby inhibiting discharge from a bladder of the person, wherein applying the patch does not comprise covering a urethra of the person with the patch.

17. The method of claim 16, for treating stress female urinary incontinence.

18. The method of claim 16, for treating urge female urinary incontinence.

19. The method of claim 16, for treating overflow female urinary incontinence.

20. The method of claim 16, for treating continuous female urinary incontinence.

21. The method of claim 16, wherein the patch comprises an adhesive layer on a side of the patch.

22. The method of claim 16, wherein the patch when applied contacts a clitoral hood of the person.

23. The method of claim 16, further comprising removing the patch from a release sheet prior to applying the patch directly to the clitoris.

* * * * *